United States Patent
Contorni et al.

(10) Patent No.: US 7,348,006 B2
(45) Date of Patent: Mar. 25, 2008

(54) VACCINES COMPRISING ALUMINIUM ADJUVANTS AND HISTIDINE

(75) Inventors: Mario Contorni, Siena (IT); Massimo Maffei, Siena (IT)

(73) Assignee: Novartis Vaccines and Diagnostics, s.r.l., Siena (IT)

( * ) Notice: Subject to any disclaimer, the term of this patent is extended or adjusted under 35 U.S.C. 154(b) by 180 days.

(21) Appl. No.: 10/484,702

(22) PCT Filed: Jul. 26, 2002

(86) PCT No.: PCT/IB02/03495

§ 371 (c)(1),
(2), (4) Date: Feb. 17, 2005

(87) PCT Pub. No.: WO03/009869

PCT Pub. Date: Feb. 6, 2003

(65) Prior Publication Data

US 2005/0158334 A1    Jul. 21, 2005

(30) Foreign Application Priority Data

Jul. 26, 2001 (GB) ................. 0118249.2
Jun. 20, 2002 (WO) ...................... PCT/IB02/03191

(51) Int. Cl.
*A61K 39/00* (2006.01)
*C07H 21/02* (2006.01)

(52) U.S. Cl. .................................. 424/184.1; 536/23.1
(58) Field of Classification Search ............. 424/184.1; 536/23.1

See application file for complete search history.

(56) References Cited

U.S. PATENT DOCUMENTS 6,472,518 B1 * 10/2002 Ribot et al. ................ 536/23.7

FOREIGN PATENT DOCUMENTS

| EP | 0835663 | 4/1998 |
|----|---------|--------|
| WO | WO 99 48525 | 9/1999 |
| WO | WO 00 57906 | 10/2000 |
| WO | WO 01 41800 | 6/2001 |

OTHER PUBLICATIONS

Hommet al: "Assessment of the Stability and Immunogenicity of Meningococcal Oligosaccharide C-CRM197 Conjugate Vaccines"; Vaccine, Butterworth Scintific. Guildford, GB, vol. 19, No. 7-8, pp. 716-725, XP004225388, Nov. 22, 2000.

* cited by examiner

*Primary Examiner*—Mark Navarro
(74) *Attorney, Agent, or Firm*—Banner & Witcoff, Ltd.

(57) ABSTRACT

To improve the stability of vaccines comprising aluminum salt(s), the invention uses the amino acid histidine. This can improve pH stability and adjuvant adsorption and can be reduce antigen hydrolysis. Histidine is preferably presen during adsorption to the aluminium salt(s). The antigen in the vaccine may be a protein or a saccharide and is preferably from *N. meningitidis*.

30 Claims, 4 Drawing Sheets

VACCINES COMPRISING ALUMINIUM ADJUVANTS AND HISTIDINE

TECHNICAL FIELD

This invention is in the field of vaccine formulation.

BACKGROUND ART

As well as containing antigenic substances, vaccines contain substances such as diluents, excipients, preservatives, stabilisers and buffers. Typically, vaccines also contain adjuvants i.e. a substance which improves the immune response raised in response to the vaccine antigen.

The adjuvants traditionally used in human vaccines have been aluminium salts such as aluminium hydroxide and aluminium phosphate. Many other experimental adjuvants are known and these are reviewed in, for instance, reference 1. Adsorption to aluminium salts remains, however, the most common vaccine adjuvant formulation.

Although their use is widespread, aluminium salts may not always be compatible with particular antigens. It has been suggested, for instance, that aluminium hydroxide may not be suitable for use in multivalent vaccines including hepatitis B virus surface antigen [2] or for use with the capsular polysaccharide from *Haemophilus influenzae* [3]. It has also been suggested that different antigens within the same vaccine formulation should be adsorbed to different aluminium salts [4] for compatibility reasons.

As well as antigen compatibility, it is necessary to consider vaccine stability when using aluminium salts. For instance, their capacity for protein adsorption has been shown to drop over time at room temperature [5] and in response to autoclaving [6]. Alum salts may also cause difficulties in freeze drying [7]. Furthermore, it has been found that aluminium hydroxide can hydrolyse saccharide antigens [8], even at low temperatures and when the antigen is conjugated to a carrier protein, thus leading to reduced efficacy.

In general, these issues only arise when attention moves to formulating an antigen for clinical use and may not be appreciated during initial research and development of the antigen itself.

It is an object of the invention to provide improvements in the stability of vaccines which include aluminium salts and, in particular, improvements in pH stability (buffering) and adjuvant adsorption at various temperatures and/or improvements in antigen stability (e.g. reduction in hydrolysis).

DISCLOSURE OF THE INVENTION

The invention is based on the surprising discovery that the amino acid histidine enhances the stability of vaccines which include aluminium salt adjuvants. This has been found both for saccharide antigens and for protein antigens.

The invention thus provides a composition comprising an antigen, an aluminium salt and histidine.

The invention also provides a process for producing this composition, comprising the step of admixing an antigen, an aluminium salt and histidine.

The Antigen

The antigen is preferably a protein antigen or a saccharide antigen (optionally conjugated). Preferred antigens are from bacteria, with the bacterial genus *Neisseria* (e.g. *N. meningitidis*) being particularly preferred.

Specific bacterial antigens for use with the invention include:

a protein antigen from *N. meningitidis* serogroup B, such as those in refs. 9 to 15, with protein '287' (see below) and derivatives (e.g. 'ΔG287') being particularly preferred, an outer-membrane vesicle (OMV) preparation from *N. meningitidis* serogroup B, such as those disclosed in refs. 16, 17, 18, 19 etc.

a saccharide antigen from *N. meningitidis* serogroup A, C, W135 and/or Y, such as the oligosaccharide disclosed in ref. 20 from serogroup C [see also ref. 21].

a saccharide antigen from *Streptococcus pneumoniae* [e.g. 22, 23, 24].

an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 25 & 26].

a diphtheria antigen, such as a diphtheria toxoid [e.g. chapter 3 of ref. 27] e.g. the $CRM_{197}$ mutant [e.g. 28].

a tetanus antigen, such as a tetanus toxoid [e.g. chapter 4 of ref. 27].

a protein antigen from *Helicobacter pylori* such as CagA [e.g. 29], VacA [e.g. 29], NAP [e.g. 30], HopX [e.g. 31], HopY [e.g. 31] and/or urease.

a saccharide antigen from *Haemophilus influenzae* B [e.g. 21], preferably oligosaccharide.

an antigen from *N. gonorrhoeae* [e.g. 9, 10, 11].

an antigen from *Chlamydia pneumoniae* [e.g. 32, 33, 34, 35, 36, 37, 38].

an antigen from *Chlamydia trachoniatis* [e.g. 39].

an antigen from *Porphyromonas gingivalis* [e.g. 40].

an antigen from *Moraxella catarrhalis* [e.g. 41].

an antigen from *Streptococcus agalactiae* (group B streptococcus) [e.g. 42, 43].

an antigen from *Streptococcus pyogenes* (group A streptococcus) [e.g. 43, 44, 45].

an antigen from *Staphylococcus aureus* [e.g. 46].

an antigen from *Bacillus anthracis* [e.g. 47, 48, 49].

Specific viral antigens for use with the invention include:

an antigen from hepatitis A virus, such as inactivated virus [e.g. 50, 51].

an antigen from hepatitis B virus, such as the surface and/or core antigens [e.g. 51, 52].

an antigen from hepatitis C virus [e.g. 53].

polio antigen(s) [e.g. 54, 55] such as IPV.

rabies antigen(s) [e.g. 56] such as lyophilised inactivated virus [e.g.57, RabAvert™].

measles, mumps and/or rubella antigens [e.g. chapters 9, 10 & 1 of ref. 27].

influenza antigen(s) [e.g. chapter 19 of ref. 27], such as the haemagglutinin and/or neuramimidase surface proteins.

an antigen from a virus in the *flaviviridae* family (genus *flavivirus*), such as from yellow fever virus, Japanese encephalitis virus, four serotypes of Dengue viruses, tick-borne encephalitis virus, West Nile virus.

a pestivirus antigen, such as from classical porcine fever virus, bovine viral diarrhoea virus, and/or border disease virus.

a parvovirus antigen e.g. from parvovirus B19.

The composition may comprise one or more of these bacterial and viral antigens. The composition may comprise no viral antigens.

Other antigens which may be used include:

a prion protein (e.g. the CJD prion protein)

an amyloid protein, such as a beta peptide [58]

a cancer antigen, such as those listed in Table 1 of ref. 59 or in tables 3 & 4 of ref. 60.

Where a saccharide or carbohydrate antigen is used, it is preferably conjugated to a carrier protein in order to enhance mimunogenicity [e.g. refs. 61 to 70]. Preferred carrier proteins are bacterial toxins or toxoids, such as diphtheria or tetanus toxoids. The $CRM_{197}$ diphtheria toxoid is particularly preferred. Other suitable carrier proteins include the *N. meningitidis* outer membrane protein [e.g. ref. 71], synthetic peptides [e.g. 72, 73], heat shock proteins [e.g. 74], pertussis proteins [e.g. 75, 76], protein D from *H. influenzae* [e.g. 77], toxin A or B from *C. difficile* [e.g. 78], etc. Where a mixture comprises capsular saccharides from both serogroups A and C, it is preferred that the ratio (w/w) of MenA saccharide: MenC saccharide is greater than 1 (e.g. 2:1, 3:1, 4:1, 5:1, 10:1 or higher). Saccharides from different serogroups of *N. meningitidis* may be conjugated to the same or different carrier proteins.

Any suitable conjugation reaction can be used, with any suitable linker where necessary.

Toxic protein antigens may be detoxified where necessary (e.g. detoxification of pertussis toxin by chemical and/or genetic means [26]).

Human papilloma virus (HPV) virus-like particles (VLPs) are not preferred antigens (cf. WO00/45841, WO00/57906, WO01/28585).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. Whole cell pertussis antigen may be used.

Antigen is preferably adsorbed to the aluminium salt.

Where HBsAg is present, preferably it is either adsorbed to aluminium hydroxyphosphate or is not adsorbed to any salt. Adsorption of HBsAg to an aluminium hydroxide is preferably avoided.

Where a *H. influenzae* saccharide antigen is present, preferably it is either adsorbed to aluminium hydroxyphosphate or is not adsorbed to any salt. Adsorption of Hib saccharides to an aluminium hydroxide is preferably avoided.

Antigens in the composition will typically be present at a concentration of at least 1 μg/ml each. In general, the concentration of any given antigen will be sufficient to elicit an immune response against that antigen.

As an alternative to using proteins antigens in the composition of the invention, nucleic acid encoding the antigen may be used [e.g. refs. 79 to 87]. Protein components of the compositions of the invention may thus be replaced by nucleic acid (preferably DNA e.g. in the form of a plasmid) that encodes the protein.

The Aluminium Salt

The aluminium salt is preferably an aluminium hydroxide (e.g. aluminium oxyhydroxide) or an aluminium phosphate (e.g. aluminium hydroxyphosphate or orthophosphate), but any other suitable salt may also be used (e.g. sulphate etc. [e.g. see chapters 8 & 9 of ref. 1]). The salt may take any suitable form (e.g. gel, crystalline, amorphous etc.). Preferred salts are (amorphous) hydroxyphosphates and (crystalline) oxyhydroxide (boehmite).

Hydroxyphosphates are obtained by precipitation and the reaction conditions and reactant concentrations during the precipitation reaction influence the degree of substitution of phosphate for hydroxyl in the salt. Hydroxyphosphates generally have a $PO_4/Al$ molar ratio between 0.3 and 0.99, and preferred salts have a ratio between 0.8 and 0.95 (e.g. 0.88±0.05). Hydroxyphosphates $[Al(OH)_x(PO_4)_y$, wherein the sum of the valence of each anion times its mole fraction is −3] can be distinguished from $AlPO_4$ by the presence of hydroxyl groups. For example, an IR spectrum band at 3146 $cm^{-1}$ (e.g. when heated to 200° C.) indicates the presence of structural hydroxyls.

Aluminium oxyhydroxide [AlO(OH)] can be distinguished from $Al(OH)_3$ by IR spectroscopy, in particular by the presence of an adsorption band at 1070 $cm^{-1}$ and a strong shoulder at 3090-3100 $cm^{-1}$.

Mixtures of different aluminium salts may also be used. It is preferred, however, to use essentially a single salt e.g. where two salts are used, the ratio of one to the other is at least 5:1 by weight e.g. at least 10:1, 100:1, 1000:1 etc.

The salt will generally be present such that the concentration of $Al^{3+}$ is at least 1 μg/ml (e.g. at least 10 μg/ml, at least 100 μg/ml etc.).

The use of histidine in combination with an aluminium phosphate (particularly a hydroxyphosphate) is particularly advantageous for acidic antigens.

The Histidine

Histidine is a standard amino acid and is readily available for use with the invention. As it is inherently biocompatible, it is safe, and thus advantageous as an component in vaccines.

The concentration of histidine in the composition will typically be at least 1 μm and at most 1M. The concentration is preferably at least 1 mM (e.g. at least 2 mM, 3 mM, 4 mM, 5 mM etc.) and is preferably at most 250 mM (e.g. at most 200 mM, 150 mM, 100 mM, 90 mM, 80 mM, 70 mM, 60 mM, 50 mM, 40 mM, 30 mM, 20 mM, 10 mM etc.). More preferably the concentration of histidine in the composition is between 2 mM and 10 mM (e.g. between 5 mM and 8 mM) and, most preferably, it is about 5 mM.

The histidine is preferably L-histidine.

The histidine preferably acts as a buffer. Histidine buffers are well known to the skilled person.

Accordingly, the histidine may be ionised within the composition of the invention.

The composition preferably has enhanced pH stability and/or reduced antigen hydrolysis when compared to an equivalent composition in which histidine buffer system is either replaced with a sodium phosphate buffer system or in which no buffer system is included. Reduced hydrolysis may be a consequence of enhanced pH stability.

Histidine may be added to the composition in the form of the amino acid itself or in the form of a salt. A typical histidine salt is the monohydrochloride monohydrate.

It will be appreciated that references to histidine in the compositions of the invention refers to 'free' histidine rather than to any histidine residues which may be part of a polypeptide (e.g. the antigen) within the composition.

Further Characteristics of the Composition

The composition is preferably in liquid form, but it may be lyophilised (cf. WO01/41800).

The composition may also comprise a sodium salt e.g. sodium phosphate or sodium chloride. The concentration of the sodium salt is preferably at least 1 mM (e.g. at least 2 mM, 3 mM, 4 mM, 5 mM etc.) and is preferably at most 10 mM (e.g. at most 10 mM, 9 mM, 8 mM, 7 mM etc.). More preferably the concentration of sodium salt in the composition is between 1 mM and 5 mM (e.g. between 2 mM and 3 mM) and, most preferably, it is about 2.5 mM.

A particular advantage of the invention is that it allows good control of pH and adsorption in vaccines which contain high concentrations of free phosphate ions, which ions may be unavoidable in the vaccine e.g. due to exchange with phosphates in the adjuvant, or due to residual phosphate buffer. Where residual phosphate ions are present at between 3 and 5 mM, for example, pH is difficult to control between 6.0 and 7.0, and some antigens tend to desorb from adjuvants, but the addition of 5 to 10 mM histidine pH and adsorption to be controlled, including during storage at elevated temperatures.

The molar ratio of histidine to free phosphate is preferably at least 1.25:1 e.g. 1.5:1, 1.75:1, 2:1, 2.25:1, 2.5:1, 3:1, 4:1 etc.

The pH of the composition is preferably between 6 and 7 (e.g. betweem 6.3 and 7.0). The pH may be maintained by the use of a buffer. This will typically be achieved inherently by the histidine in the composition.

The composition will not, in general, contain: serum (e.g. fetal calf serum etc.) or other such components used in cell culture; host cell DNA at a level of greater than 100 pg/dose for antigens purified from cell culture; living cells.

The composition will generally be sterile and/or pyrogen-free.

The composition may comprise a detergent (e.g. a Tween, such as Tween 80) in order to minimise adsorption of antigens to containers.

The composition preferably does not comprise a preservative. Where a preservative is present, mercurial preservatives (e.g. thimerosal) may be used (cf. WO98/34594). Preservatives which may be present or absent are 2-phenoxy-ethanol, methyl parabens, propyl parabens and benzyl alcohol (or mixtures thereof).

Immunogenic Compositions and Medicaments

The composition of the invention is typically a vaccine composition.

The invention also provides a composition of the invention for use as a medicament. The medicament is preferably able to raise an immune response in a mammal against the antigen (i.e. it is an immunogenic composition) and is more preferably a vaccine.

The invention also provides the use of a composition of the invention in the manufacture of a medicament for raising an immune response in a mammal against the antigen. The medicament is preferably a vaccine.

The invention also provides a method for raising an immune response in a mammal comprising the step of administering an effective amount of a composition of the invention. The immune response is preferably protective. The method may raise a booster response.

The mammal is preferably a human, and most preferably a child.

These uses and methods are preferably for the prevention and/or treatment of a disease caused by a *Neisseria* (e.g. meningitis, septicaemia; gonorrhoea etc.), by *H. influenzae* (e.g. otitis media, bronchitis, pneumonia, cellulitis, pericarditis, meningitis etc.) or by pneumococcus (e.g. meningitis, sepsis, pneumonia etc). The prevention and/or treatment of bacterial meningitis is thus preferred.

Vaccines according to the invention may either be prophylactic (i.e. to prevent infection) or therapeutic (i.e. to treat disease after infection), but will typically be prophylactic.

Further Components of the Composition

The composition of the invention will typically, in addition to the components mentioned above, comprise one or more 'pharmaceutically acceptable carriers', which include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, trehalose (WO00/56365) and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. A thorough discussion of pharmaceutically acceptable excipients is available in *Remington's Pharmaceutical Sciences* [e.g. ref. 88].

Immunogenic compositions used as vaccines comprise an immunologically effective amount of antigen, as well as any other of the above-mentioned components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Dosage treatment may be a single dose schedule or a multiple dose schedule (e.g. including booster doses). The vaccine may be administered in conjunction with other immunoregulatory agents.

The vaccine may be administered in conjunction with other immunoregulatory agents.

The vaccine may include an adjuvant in addition to the aluminium salt. Preferred adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (WO90/14837; Chapter 10 in ref. 1), containing 5% Squalene, 0.5% Tween 80, and 0.5% Span 85 (optionally containing MTP-PE) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (2) saponin adjuvants, such as QS21 or Stimulon™ (Cambridge Bioscience, Worcester, Mass.) may be used or particles generated therefrom such as ISCOMs (immunostimulating complexes), which ISCOMS may be devoid of additional detergent e.g. WO00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2220221, EP-A-0689454; (6) combinations of 3dMPL with, for example, QS21 and/or oil-in-water emulsions e.g. EP-A-0835318, EP-A-0735898, EP-A-0761231; (7) oligonucleotides comprising CpG motifs [Krieg Vaccine 2000, 19, 618-622; Krieg *Curr opin Mol Ther* 2001 3:15-24; Roman et al., *Nat. Med.*, 1997, 3, 849-854; Weiner et al., *PNAS USA*, 1997, 94, 10833-10837; Davis et al., *J. Immunol.*, 1998, 160, 870-876; Chu et al., *J. Exp. Med.*, 1997, 186, 1623-1631; Lipford et al., *Eur. J. Immunol.*, 1997, 27, 2340-2344; Moldoveanu et al., *Vaccine*, 1988, 16, 1216-1224, Krieg et al., *Nature*, 1995, 374, 546-549; Klinman et al., *PNAS USA*, 1996, 93, 2879-2883; Ballas et al., *J. Immunol.*, 1996, 157, 1840-1845; Cowdery et al., *J. Immunol.*, 1996, 156, 4570-4575; Halpern et al., *Cell. Immunol.*, 1996, 167, 72-78; Yamamoto et al., *Jpn. J. Cancer Res.*, 1988, 79, 866-873; Stacey et al., *J. Iimmunol.*, 1996, 157, 2116-2122; Messina et al., *J. Immunol.*, 1991, 147, 1759-1764; Yi et al., *J. Immunol.*, 1996, 157, 4918-4925; Yi et al., *J. Immunol.*, 1996, 157, 5394-5402; Yi et al., *J. Iiizmuolno.*, 1998, 160, 4755-4761; and Yi et al., *J. Immunol.*, 1998, 160, 5898-5906; International patent applications WO96/02555, WO98/16247, WO98/18810, WO98/40100, WO98/55495, WO98/37919 and WO98/52581] i.e. containing at least one CG dinucleotide, with 5-methylcytosine optionally being used in place of cytosine; (8) a polyoxyethylene ether or a polyoxyethylene ester e.g. WO99/52549; (9) a polyoxyethylene sorbitan ester surfactant in combination with an octoxynol (e.g. WO01/21207) or a polyoxyethylene alkyl ether or ester surfactant in combination with at least one additional non-ionic surfactant such as an octoxynol (e.g. WO01/21152); (10) an immunostimulatory oligonucleotide (e.g. a CpG oligonucleotide) and a saponin e.g. WO00/62800; (11) an immunostimulant and a particle of metal salt e.g. WO00/23105; (12) a saponin and an oil-in-water emulsion e.g. WO99/11241; (13) a saponin (e.g. QS21)+3dMPL+IL-12 (optionally+a sterol) e.g. WO98/57659; (14) chitosan; (15) cholera toxin or *E. coli* heat labile toxin, or detoxified mutants thereof [89]; (16) microparticles of poly(α-hydroxy)acids, such as PLG; (17) other substances that act as immunostimulating agents to enhance the efficacy of the composition.

Muramyl peptides include N-acetyl-muramyl-L-threonyl-D-isoglutamine (thr-MDP), N-acetylnormuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine MTP-PE), etc.

Once formulated, the compositions of the invention can be administered directly to the subject. The subjects to be treated can be animals; in particular, human subjects can be treated. The vaccines are particularly useful for vaccinating children and teenagers.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect. Direct delivery of the compositions will generally be parenteral (e.g. by injection, either subcutaneously, intraperitoneally, intravenously or intramuscularly or delivered to the interstitial space of a tissue). The compositions can also be administered into a lesion. Other modes of administration include oral and pulmonary administration, suppositories, and transdermal or transcutaneous applications (e.g. see WO98/20734), needles, and hyposprays. Dosage treatment may be a single dose schedule or a multiple dose schedule (e.g. including booster doses).

The Step of Admixing Antigen, Aluminium Salt and Histidine

To make compositions of the invention, antigen, aluminium salt and histidine must be combined. It is preferred that, when the antigen and aluminium salt are mixed, the histidine should be present. Histidine is thus present during adsorption to the aluminium salt. This compares with adding histidine to an antigen/aluminium salt combination which already exists i.e. the histidine in the process is not simply added as a buffer after antigen and aluminium salt have interacted, but instead it is present during their interaction.

In the process of the invention, therefore, antigen is preferably admixed with a histidine/aluminium salt mixture. The process of the invention may therefore comprise the following steps: (a) preparing a mixture of the aluminium salt and the histidine; and (b) admixing the antigen with said mixture. The mixture of (a) is preferably aqueous and may be prepared in aqueous conditions or may be a dried mixture which is re-hydrated prior to use.

Once one or more antigens has been adsorbed to an aluminium salt in the presence of histidine, the mixture may be combined with other antigens e.g. combined with existing diphtheria, tetanus, pertussis, polio or hepatitis B virus compositions.

Definitions

The term "comprising" means "including" as well as "consisting" e.g. a composition "comprising" X may consist exclusively of X or may include something additional e.g. X+Y.

The term "about" in relation to a numerical value x means, for example, x±10%.

MODES FOR CARRYING OUT THE INVENTION

EXAMPLE 1 pH Stability and Adsorption of Menigococcal B '287' Antigen

Reference 11 discloses a protein antigen named '287' from *N. meningitidis* serogroup B. Reference 90 discloses a form of this antigen ('ΔG287') which is truncated to remove the N-terminal amino acids up to and including its hexaglycine region. 287 and ΔG287 are both able to elicit a protective immune response in mice. References 16 to 19 disclose OMV antigens from *N. meningitidis* serogroup B. These OMVs are also able to elicit a protective immune response in mice.

These two antigens were formulated by adsorption to aluminium oxyhydroxide adjuvant. Two adjuvant concentrations (1 mg/ml and 3.3 mg/ml) were tested.

Immunisation studies in mice showed that vaccine immunogenicity is linked to the level of adsorption of the antigens to the adjuvant. To assess adsorption levels, samples of the final formulations were centrifuged at 1300 rpm for 10 minutes and the supernatant was analysed by SDS-PAGE in order to detect the presence of non-adsorbed antigen. The relevant protein standards at an appropriate concentration were loaded adjacent for quantitative comparison.

Figure 1:
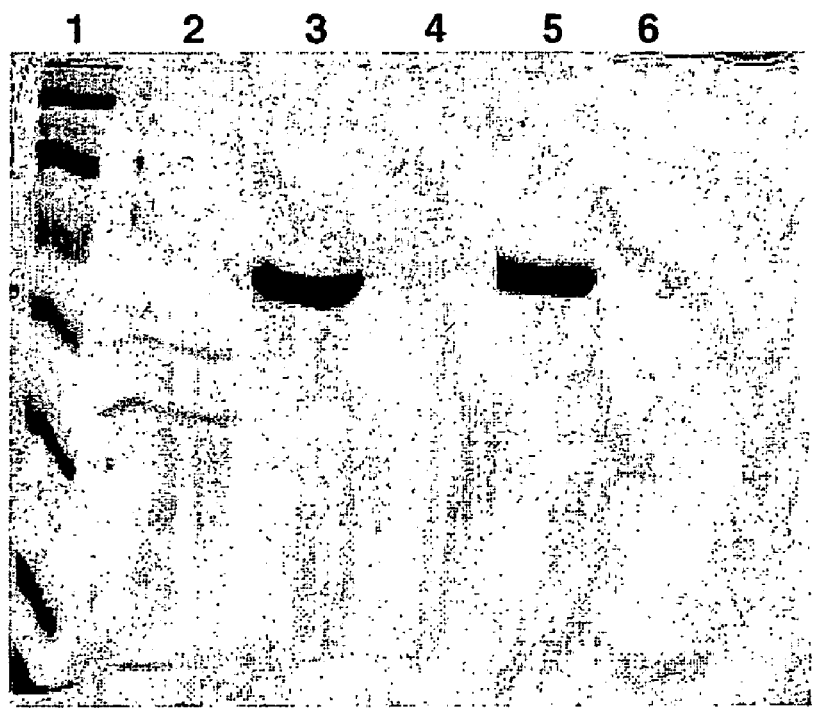
FIG. 1 shows SDS-PAGE analysis of antigenic compositions following centrifugation. Lane 1 includes MW markers (220, 97, 66, 46, 30, 21, 14 kDa). OMV antigen (2 μkg) was used in lane 2; ΔG287 antigen was used in lanes 3 (10 μg) and 4 (0.5 μg). The antigen used in lanes 5 and 6 combination of OMV (50 μg/ml) and ΔG287 (100 μg/ml) with 1 mg/ml aluminium oxyhydroxide; the lane 5 composition included 10 mM sodium phosphate (PBS), whereas the lane 6 composition included 5 mM histidine in saline solution.

In order to maintain a stable physiological pH at 4° C. and 37° C. over a period of 4 weeks using sodium phosphate buffer it was found that the composition requires 10 mM sodium phosphate. At this level, however, adsorption of ΔG287 was only 50% (FIG. 1, lane 5). 100% adsorption could be maintained at 2.5 mM sodium phosphate (Lanes 5 of FIGS. 2 & 3), but this composition does not have a stable pH at either 4° C. or 37° C.

It was therefore necessary to find an alternative buffer system which would maintain pH stability without decreasing adsorption.

Figure 2:
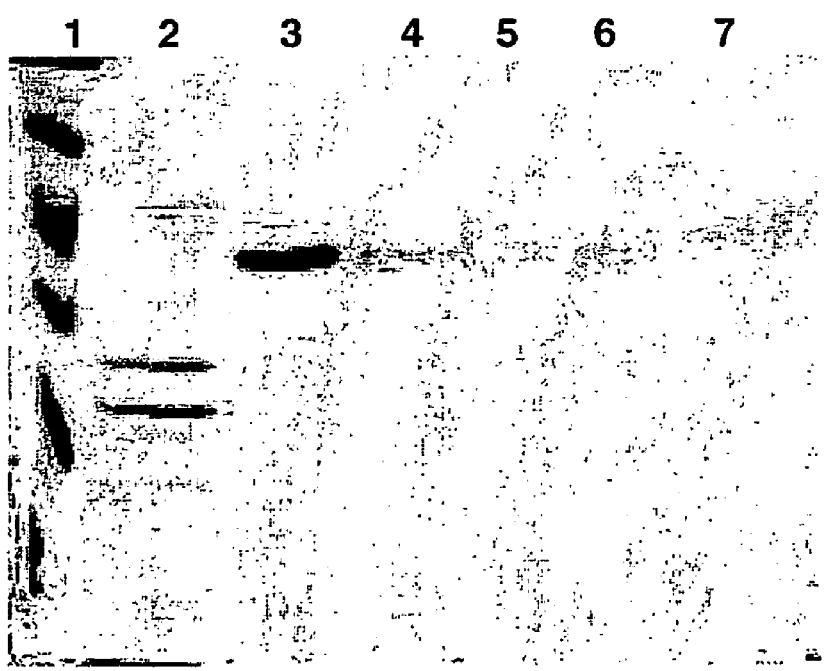
FIG. 2 also shows SDS-PAGE analysis of antigenic compositions following centrifugation. Lane 1 includes the same MW markers as FIG. 1. OMV antigen (2.5 μg) was used in lane 2; ΔG287 antigen was used in lanes 3 (2 μg) and 4 (0.5 μg). The antigen used in lanes 5, 6 and 7 was a combination of OMV (50 μg/ml) and ΔG287 (100 μg/ml) with 1 mg/ml aluminium oxyhydroxide in saline solution (pH 6.5); the lane 5 composition included 2.5 mM sodium phosphate, the lane 6 composition included 5 mM histidine, and the lane 7 composition included 10 mM histidine.
Figure 3:
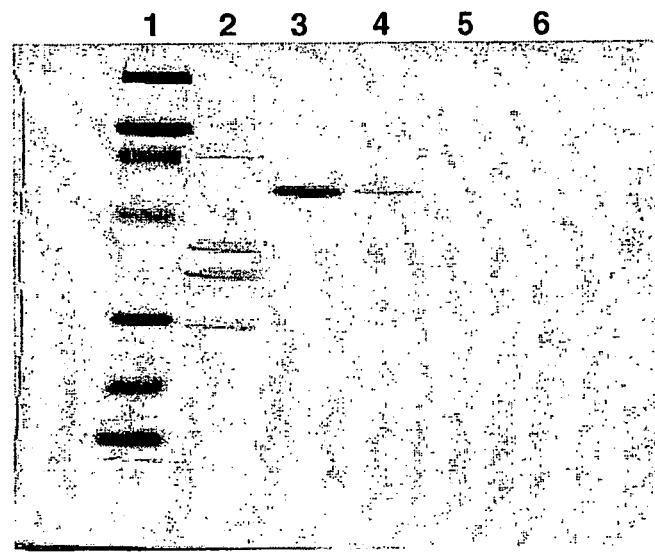
FIG. 3 also shows SDS-PAGE analysis of antigenic compositions following centrifugation. Lane 1 includes the same MW markers as FIG. 1. OMV antigen (2 μkg) was used in lane 2; ΔG287 antigen was used in lanes 3 (2 μg) and 4 (0.5 μg). The antigen used in lanes 5 and 6 was a combination of OMV (50 μg/ml) and ΔG287 (100 μg/ml) with 3.3 mg/ml aluminium oxyhydroxide in saline solution (pH 6.5); the lane 5 composition included 2.5 mM sodium phosphate (PBS), whereas the lane 6 composition included 5 mM histidine in saline solution.

Adsorption was 95-100% using 5 mM histidine (Lanes 6 of FIGS. 1, 2 & 3) and also using 10 mM histidine (FIG. 2, lane 7). In terms of adsorption, therefore, 5 mM or 10 mM histidine was equivalent to 2.5 mM sodium phosphate in the presence of either 1 mg/ml (FIGS. 1 & 2) or 3.3 mg/ml (FIG. 3) aluminium oxyhydroxide.

In order to define the pH range in which the vaccine compositions are stable, three starting pH values were chosen (pH 6.0, 6.5 and 7.0) and pH stability was monitored over four weeks in the presence of either 2.5 mM sodium phosphate or 5 mM histidine. Stability was monitored at both 4° C. and 37° C.

The antigen in all vaccines was a combination of ΔG287 (100 μg/ml) and OMV (50 μg/ml) adjuvanted with 3.3 mg/ml aluminium oxyhydroxide.

Figure 4:
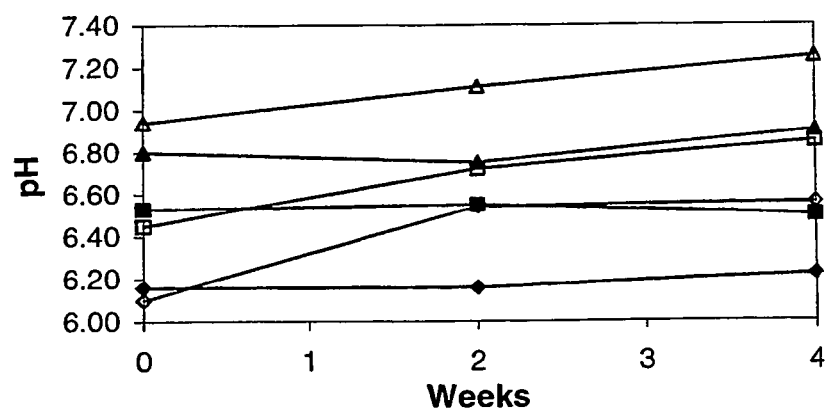
FIG. 4 shows the pH stability of vaccine formulations at 4° C. Filled symbols represent vaccines buffered with 5 mM histidine; open symbols represent vaccines buffered with 2.5 mM sodium phosphate. The initial pH was 6.0 (diamond), 6.5 (square) or 7.0 (triangle).
Figure 5:
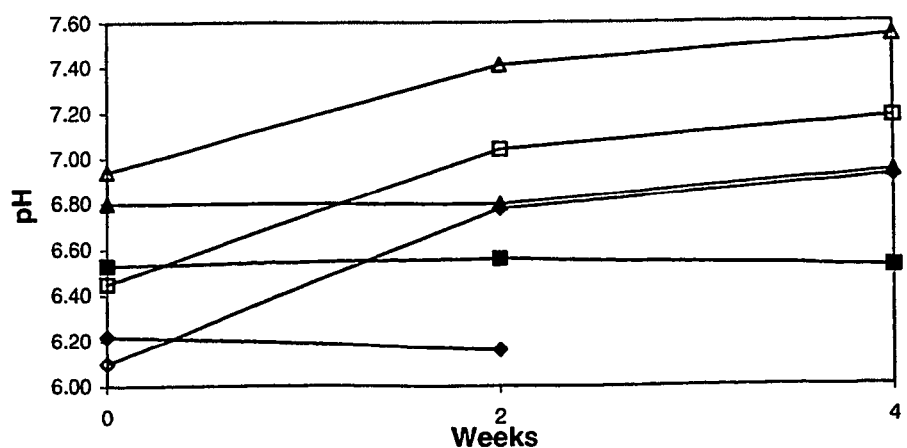
FIG. 5 shows the same at 37° C.

FIG. 4 shows pH stability at 4° C. and FIG. 5 shows pH stability at 37° C. [NB—due to bacterial contamination, no measurement of the pH 6.0 histidine-buffered vaccine was possible at 4 weeks].

At both temperatures the pH tended to increase over time with 2.5 mM sodium phosphate buffer but was stable in the presence of 5 mM histidine buffer.

A In comparison with sodium phosphate buffer, therefore, the use of histidine offers pH stability over time without reducing adsorption.

EXAMPLE 2

Adsorption of Meningococcal C Saccharide Antigen

Saccharide conjugates tend to degrade by hydrolysis [7,8] when present in solution ('liquid' vaccines). Conjugates can be lyophilised to avoid this [7], but this requires adjuvant to be added at the point of reconstitution. It would be preferable to have a liquid form of the vaccine in which the saccharide is not subject to hydrolytic degradation.

This was investigated for a conjugate of meningococcus serogroup C oligosaccharide on CRM$_{197}$ carrier protein [20]. CRM$_{197}$ is acidic and thus does not completely adsorb to negatively charged aluminium phosphates. Histidine, however, is positively charged and it was thought that this might be able to mask the negative charge. Histidine buffer was thus tested with the aim of improving adsorption of MenC-CRM$_{197}$ to aluminium hydroxyphosphate.

Antigen adsorption was evaluated in the presence and absence of histidine buffer by measuring protein concentration in the vaccine supernatant using the BCA protein assay, after centrifugation to separate the adjuvant pellet. The vaccines were formulated as 20 μg/ml oligosaccharide and 454 μg/ml CRM$_{197}$ protein. Results were as follows:

| Antigen | Adjuvant | [Histidine] (mM) | Protein (μg/ml) |
|---|---|---|---|
| MenC-CRM$_{197}$ | Hydroxyphosphate Al$^{3+}$ = 0.6 mg/ml | 0 | 42.4 |
| | | 5 | 28.6 |
| | | 10 | 21.7 |

Antigen adsorption thus improves when histidine is present in the formulation: adsorption is about 6% in the absence of histidine; 5 mM histidine increases this to 36%; 10 mM histidine increases adsorption to almost 52%.

Histidine is thus a useful additive for improving the adsorption of antigens to aluminium hydroxyphosphate.

EXAMPLE 3

Adsorption of Meningococcal B NadA Antigen

NadA (Neisserial adhesin A) from serogroup B *N. meningitidis* is disclosed as protein '961' in ref. 11 (SEQ IDs 2943 & 2944) and as 'NMB1994' in ref. 13 (see also GenBank accession numbers 11352904 & 7227256). Allelic forms of NadA are disclosed in reference 91. Preferred forms of NadA lack the C-terminus anchor domain ('961c').

Figure 8:
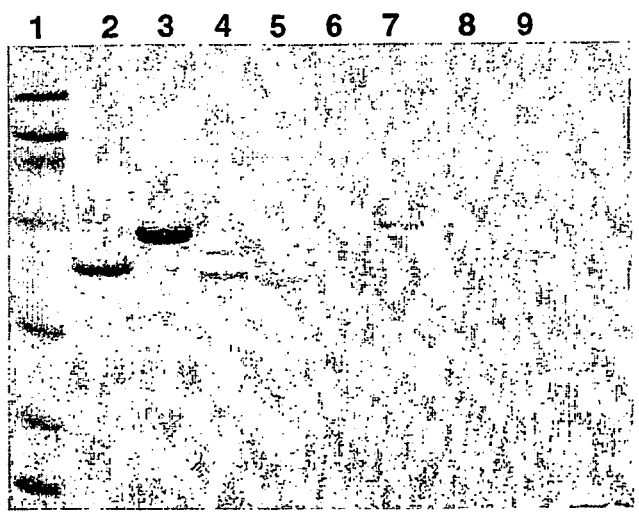
FIG. 8 shows a SDS-PAGE gel for various antigens. Lane 1 contains MW markers. Lanes 2 to 5 contain markers: (2) 961c; (3) 936-741; (4) New Zealand OMVs; and (5) Norwegian OMVs. Lanes 6 to 9 show supernatants of centrifuged histidine formulations of the invention after 1 month storage at 2-8° C.: (6) 961c; (7) 936-741; (8) OMV$_{NZ}$; (9) OMV$_{Norway}$.
Figure 9:
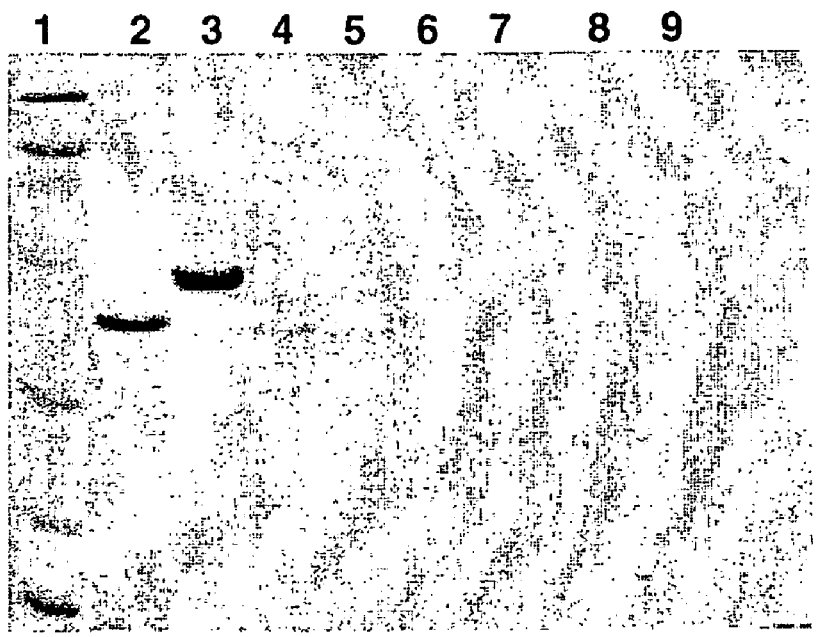
FIG. 9 shows the same as FIG. 8, but lanes 6-9 are after storage at 36-38° C.

961c (100 μg/ml) was adsorbed onto aluminium oxyhydroxide (3 mg/ml) in the presence of 10 mM histidine buffer, pH 6.5. After 4 weeks of storage at either 2-8° C. or at 36-38° C., the antigen remained 100% adsorbed (FIGS. 8 & 9, lane 6). The pH of the composition was 6.44 at time zero and after 4 weeks of storage rose very slightly to 6.48 (2-8° C.) or 6.47 (36-38° C.).

EXAMPLE 4

Adsorption of Meningococcal B Hybrid Antigens

Figure 6:
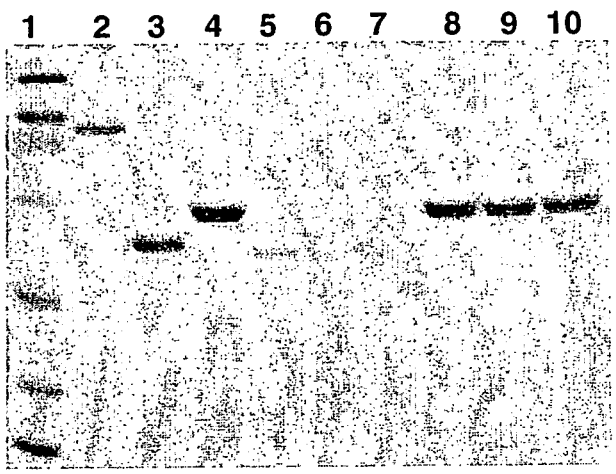
FIG. 6 shows a SDS-PAGE gel for various antigens. Lane 1 contains MW markers. Lanes 2 to 6 contain markers: (2) ΔG287-953; (3) 961c; (4) 936-741; (5) New Zealand OMVs; and (6 Norwegian OMVs. Lanes 7 to 10 show supernatants of centrifuged histidine formulations of the invention after 1 month storage at 2-8° C.: (7) ΔG287-953; (8) 961c+936-741+ΔG287-953; (9) 961c+936-741+ΔG287-953+OMV$_{NZ}$; (10) 961c+936-741+ΔG287-953+OMV$_{Norway}$.
Figure 7:
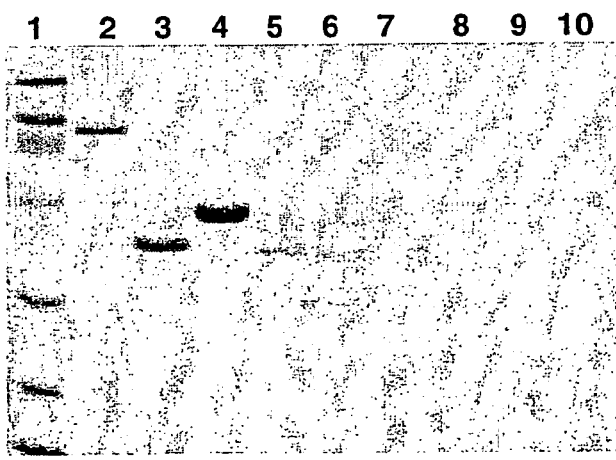
FIG. 7 shows the same as FIG. 6, but lanes 7-10 are after storage at 36-38° C.

References 92 & 93 disclose hybrid expression of meningococcal B antigens. One such hybrid is 'ΔG287$_{nz}$-953' and another is '936-741'. These two hybrids (100 μg/ml) were each adsorbed onto aluminium oxyhydroxide (3 mg/ml) in the presence of 10 mM histidine buffer, pH 6.3. After 4 weeks of storage at either 2-8° C. or at 36-38° C., 'ΔG287$_{nz}$-953' remained 100% adsorbed (FIGS. 6 & 7, lane 7), with pH rising slightly from 6.44 to 6.52 (2-8° C.) or 6.53 (36-38° C.). '936-741' remained 100% adsorbed at 36-38° C. (FIG. 9, lane 7) but was ~99% adsorbed at 2-8° C. (FIG. 8, lane 7), with pH rising slightly from 6.33 to 6.37 (2-8° C.) or 6.38 (36-38° C.).

EXAMPLE 5

Adsorption of Menizzgococcal OMVs

As mentioned above, OMV vaccines from meningococcus B are well known. OMVs were prepared from the Norwegian strain of meningococcus B or from a New Zealand strain (394/98). These two OMV preparations (50 μg/ml) were adsorbed onto aluminium oxyhydroxide (3 mg/ml) in the presence of 10 mM histidine buffer, pH 6.5. After 4 weeks of storage at either 2-8° C. or at 36-38° C., both OMV preparations remained 100% adsorbed (FIGS. 8 & 9, lanes 8 & 9). For the Norwegian OMVs, pH rose slightly from 6.39 to 6.42 over 4 weeks at both storage temperatures. For the New Zealand OMVs, pH rose slightly from 6.40 to 6.42 (2-8° C.) or 6.43 (36-38° C.).

New Zealand OMVs were alternatively formulated with 5 mM histidine. Starting with pure water, the aluminium oxyhydroxide was added, followed by histidine, with 10 minutes mixing. The OMVs were then added and mixed for 15 minutes. NaCl was then added followed by 10 minutes further mixing. The final composition was 3.3 mg/ml aluminium oxyhydroxide, 7.5 mM NaCl, 5 mM histidine, 100 μg/ml OMV, pH 6.42.

During storage at either 2-8° C. or 36-36° C., pH and OMV adsorption varied as follows:

| | pH | | % Adsorption | |
|---|---|---|---|---|
| | 2-8° C. | 36-38° C. | 2-8° C. | 36-38° C. |
| Time zero | 6.42 | 6.42 | 100 | 100 |
| 15 days | 6.36 | 6.37 | 100 | 100 |
| 30 days | 6.35 | 6.34 | 100 | 100 |

Figure 10:
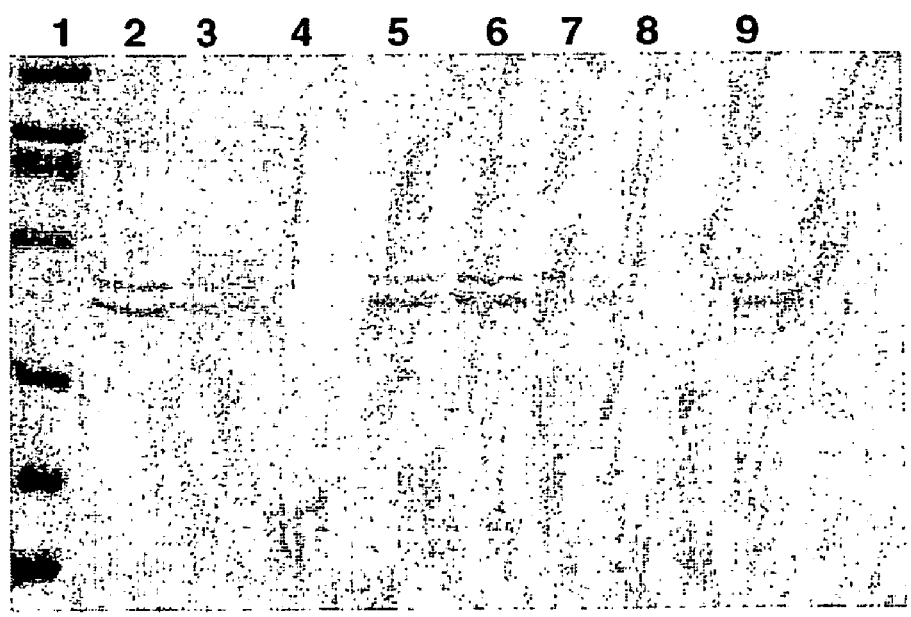
FIG. 10 shows a SDS-PAGE gel for New Zealand OMVs. Lane 1 contains MW markers. Lanes 2, 3, 6 & 7 contain OMV markers stored at either 2-8° C. (lanes 2 & 3) or 36-38° C. (lanes 6 & 7), present at either 2 μg lanes 2 & 6) or 1 μg (lanes 3 & 7). Lanes 4, 5, 8 & 9 show OMVs in histidine formulations of the invention after 30 days storage at either 2-8° C. (lanes 4 & 5) or 36-38° C. (lanes 8 & 9). Lanes 4 & 8 show supernatant of centrifuged OMVs, whereas lanes 5 & 9 show pellets.

A comparison of lanes 4 & 5 (2-8° C.) or lanes 8 & 9 (36-38° C.) in FIG. 10 shows that OMVs remain adsorbed after 1 month of storage.

EXAMPLE 6

Adsorption of Mixtures of Meningococcal OMVs and Protein Antigens

961c, ΔG287$_{nz}$-953 and 936-741 were mixed at 100 μg/ml of each antigen and the mixture was adsorbed onto aluminium oxyhydroxide (3 mg/ml) in the presence of 10 mM histidine buffer, pH 6.3. In two further formulations, OMVs were included (50 μg/ml) from either Norwegian or New Zealand strain meningococcus B.

All antigens in the three mixtures (FIGS. 6 & 7, lanes 8-10) showed 100% adsorption after 4 weeks of storage at either 2-8° C. or at 36-38° C., except for 936-741 which was ~96% adsorbed in all three mixtures at 2-8° C. and ~99% adsorbed at 36-38° C. The pH of each of the three mixtures rose slightly from 6.53 at time zero to 6.62 after 4 weeks at 2-8° C. At 36-38° C., the pH of three mixtures rose to 6.71±0.02.

The individual antigens brought residual phosphate ions into the mixture from their own PBS. Phosphate ions were sometimes present at between 3 and 5 mM in the combined antigen mixture. In the presence of these high concentrations of residual phosphate buffer, it was difficult to stabilise pH within 6.0 to 7.0, even with 5 mM histidine. When histidine was increased to 10 mM, however, pH was stabilised. Furthermore, the antigens remained adsorbed even after 1 month of storage at either 2-8° C. or at 36-38° C.

EXAMPLE 7

Adsorption of Meningococcal A Saccharide Antigen

Reference 94 discloses CRM$_{197}$ conjugates of capsular oligosaccharide from serogroup A meningococcus. The conjugates are not fully stable and are therefore prepared in lyophilised form, ready for re-constitution at the time of administration. The lyophilised form was prepared to have components which give the following composition after reconstitution into a unit dose:

| Component | Concentration |
|---|---|
| CRM-MenA | 20 μg saccharide/ml |
| Potassium phosphate buffer | 5 mM |
| Mannitol | 15 mg/ml |

This composition has no adjuvant, so an adjuvant was prepared for its reconstitution:

| Component | Concentration |
|---|---|
| Aluminium oxyhydroxide | 0.68 mg Al$^{3+}$/ml |
| Histidine buffer | 10 mM |
| Sodium chloride | 9 mg/ml |
| Tween 80 | 0.005% |
| PH | 7.2 ± 0.05 |

* amorphous hydroxyphosphate, PO$_4$/Al molar ratio between 0.84 and 0.92

EXAMPLE 8

Adsorption of Meningococcal C, W135 and Y Saccharide Antigens

Reference 94 discloses CRM$_{197}$ conjugates of capsular oligosaccharides from meningococcus serogroups C, W135 and Y. A trivalent mixture of the three conjugates either adsorbed onto an aluminium oxyhydroxide adjuvant (2 mg/ml) or an aluminium hydroxyphosphate adjuvant (0.6 mg/ml Al$^{3+}$) was prepared. The compositions of the two trivalent mixtures were as follows:

| Component | Concentration | Concentration |
|---|---|---|
| Aluminium oxyhydroxide | 0.68 mg Al$^{3+}$/ml | — |
| Aluminium hydroxyphosphate* | — | 0.6 mg Al$^{3+}$/ml |
| CRM-MenC | 20 μg saccharide/ml | 20 μg saccharide/ml |
| CRM-MenY | 20 μg saccharide/ml | 20 μg saccharide/ml |
| CRM-MenW135 | 20 μg saccharide/ml | 20 μg saccharide/ml |
| Sodium phosphate buffer | — | 10 mM |
| Histidine buffer | 10 mM | — |
| Sodium chloride | 9 mg/ml | 9 mg/ml |
| Tween 80 | 0.005% | 0.005% |

*amorphous hydroxyphosphate, PO$_4$/Al molar ratio between 0.84 and 0.92

For the oxyhydroxide/histidine formulation, stability of the saccharide components either in the bulk mixture or after packaging into vials was as follows:

| | Stored at 2-8° C. | | Stored at 36-38° C. | |
|---|---|---|---|---|
| Time (days) | Free saccharide (μg/ml) | Free saccharide % | Free saccharide (μg/ml) | Free saccharide % |
| MenC bulk | | | | |
| 0 | <1.2 | <6 | <1.2 | <6 |
| 15 | <1.2 | <6 | <1.2 | <6 |
| 30 | <1.2 | <6 | <1.2 | <6 |
| MenC vials | | | | |
| 0 | <1.2 | <6 | <1.2 | <6 |
| 15 | <1.2 | <6 | <1.2 | <6 |
| 30 | <1.2 | <6 | 1.3 | 6.6 |
| MenW135 bulk | | | | |
| 0 | 2.5 | 12.5 | 2.5 | 12.5 |
| 15 | 2.3 | 11.4 | 3.4 | 16.8 |
| 30 | 2.3 | 11.5 | 3.5 | 17.3 |
| MenW135 vials | | | | |
| 0 | 2.1 | 10.6 | 2.1 | 10.6 |
| 15 | 2.3 | 11.7 | 2.7 | 13.3 |
| 30 | 20. | 10.2 | 3.3 | 16.3 |
| MenY bulk | | | | |
| 0 | 1.7 | 8.3 | 1.7 | 8.3 |
| 15 | <1.3 | <6.3 | 2.0 | 10.2 |
| 30 | 1.3 | 6.3 | 2.4 | 12.2 |
| MenY vials | | | | |
| 0 | 1.4 | 7.1 | 1.4 | 7.1 |
| 15 | 1.5 | 7.6 | 2.1 | 10.7 |
| 30 | 1.3 | 6.3 | 2.9 | 14.3 |

Free saccharide levels are thus stable for at least 1 month at 2-8° C., before and after packaging.

Under thermal stress conditions, small increases in free saccharide are seen over time for MenW135 and MenY, but MenC remains stable.

Over the 30 days, pH in vials and bulk was stable at 7.15±0.05 at both storage temperatures.

EXAMPLE 9

Adsorption of Menizgococcal A, C, W135 and Y Saccharide Antigens

The two trivalent liquid compositions of example 8 were diluted and 0.5 ml used to reconstitute the lyophilised MenA conjugate of example 7. The resulting tetravalent mixture was administered to ten Balb/c mice (female 6-8 weeks old) per group by subcutaneous injection at day 0 and 28. The mixture contained 2 μg of each saccharide conjugate per dose, which represents ⅕ of the single human dose (SHD). Controls were saline or unconjugated homologous polysaccharides. Bleedings were performed before immunization and then at day 42, with sera stored at −70° C.

All the conjugates used were safe and immunogenic in the animals. GMT post-II ELISA titres (with 95% confidence intervals) were as follows:

| Vaccine | Adjuvant | A | Y | W135 | C |
|---|---|---|---|---|---|
| MenA (lyophilised and resuspended) | Hydroxyphosphate | 172 (69-439) | — | — | — |
| | Oxyhydroxide | 619 (419-906) | — | — | — |
| MenY | Hydroxyphosphate | — | 328 (147-731) | — | — |
| | Oxyhydroxide | — | 452 (344-593) | — | — |
| MenW | Hydroxyphosphate | — | — | 80 (28-225) | — |
| | Oxyhydroxide | — | — | 277 (185-411) | — |
| MenC | Hydroxyphosphate | — | — | — | 317 (152-659) |
| | Oxyhydroxide | — | — | — | 723 (615-851) |
| MenA (lyophilized) + MenC, W135, Y | Hydroxyphosphate | 32 (15-68) | 397 (252-627) | 99 (35-288) | 114 (53-246) |
| | Oxyhydroxide | 206 (112-372) | 141 (97-205) | 139 (76-251) | 163 (122-218) |

Typically, therefore, titres are higher in the aluminium oxyhydroxide+histidine groups. Serum bactericidal titres were also generally better in the aluminium oxyhydroxide+histidine groups.

In parallel experiments, mice were immunised as described above but the vaccine compositions contained different ratios of the various oligosaccharide conjugates. Lyophilised MenA oligo-conjugate was used in all experiments. ELISA titres were as follows:

| Antigen quantity (μg/dose) | | | | Aluminium | GMT ELISA (95% confidence interval) | | | |
|---|---|---|---|---|---|---|---|---|
| A | C | W135 | Y | adjuvant | A | C | W135 | Y |
| 4 | 2 | 2 | 2 | Hydroxyphosphate | 177 (107-291) | 367 (263-510) | 239 (135-424) | 239 (184-311) |
| 4 | 2 | 2 | 2 | Oxyhydroxide | 390 (313-486) | 494 (345-706) | 338 (266-430) | 158 (96-260) |
| 2 | 2 | 2 | 2 | Hydroxyphosphate | 132 (59-296) | 582 (268-1155) | 143 (75-272) | 247 (152-400) |
| 2 | 2 | 2 | 2 | Oxyhydroxide | 337 (239-476) | 569 (462-679) | 171 (117-251) | 100 (59-169) |

A second set of experiments was performed using a dosage of 2 μg/ml saccharide for MenA and MenC, half that dosage for MenY, and a quarter dosage for MenW135. ELISA titres were as follows:

| Antigen quantity (μg/dose) | | | | Aluminium | GMT ELISA (95% confidence interval) | | | |
|---|---|---|---|---|---|---|---|---|
| A | C | W135 | Y | adjuvant | A | C | W135 | Y |
| 2 | 2 | 2 | 2 | Hydroxyphosphate | 32 (15-68) | 114 (53-246) | 99 (35-288) | 397 (252-627) |
| | | | | Oxyhydroxide | 206 (112-372) | 163 (122-218) | 139 (76-251) | 141 (97-205) |
| 2 | 2 | 1 | 0.5 | Hydroxyphosphate | 96 (49-187) | 238 (101-561) | 42 (20-89) | 315 (114-867) |
| | | | | Oxyhydroxide | 293 (144-597) | 267 (158-451) | 83 (43-163) | 244 (152-392) |

At least for serogroups A, C and W135, therefore, the oxyhydroxide+histidine formulation generally gives better titres than hydroxyphosphate at these different antigen ratios.

It will be understood that the invention has been described by way of example only and modifications may be made whilst remaining within the scope and spirit of the invention.

REFERENCES (THE CONTENTS OF WHICH ARE HEREBY INCORPORATED BY REFERENCE)

1—Vaccine Design: *subunit & adjuvant approach* (1995) Powell & Newman (ISBN: 030644867X)
2—International patent application WO93/24148.
3—International patent application WO97/00697.
4—International patent application WO98/48525.
5—Burrell et al. (2000) *Vaccine* 18:2188-2192.
6—Burrell et al. (1999) *Vaccine* 17:2599-2603.
7—Corbel (1996) *Dev Biol Stand* 87:113-124.
8—Sturgess et al. (1999) *Vaccine* 17:1169-1178.
9—International patent application WO99/24578.
10—International patent application WO99/36544.
11—International patent application WO99/57280.
12—International patent application WO00/22430.
13—Tettelin et al. (2000) *Science* 287:1809-1815.
14—International patent application WO96/29412.
15—Pizza et al. (2000) *Science* 287:1816-1820.
16—International patent application WO01/52885.
17—Bjune et al. (1991) *Lancet* 338 (8775):1093-1096.
18—Fukasawa et al. (1999) *Vaccine* 17: 2951-2958.
19—Rosenqvist et al. (1998) *Dev. Biol. Stand.* 92:323-333.
20—Costantino et al. (1992) *Vaccine* 10:691-698.
21—Costantino et al. (1999) *Vaccine* 17: 1251-1263.
22—Watson (2000) *Pediatr Infect Dis J* 19:331-332.
23—Rubin (2000) *Pediatr Clin North Am* 47:269-285, v.
24—Jedrzejas (2001) *Microbiol Mol Biol Rev* 65:187-207.
25—Gustafsson et al. (1996) *N. Engl. J. Med.* 334:349-355.
26—Rappuoli et al. (1991) *TIBTECH* 9:232-238.
27—*Vaccines* (1988) eds. Plotkin & Mortimer. ISBN 0-7216-1946-0.
28—Del Guidice et al. (1998) *Molecular Aspects of Medicine* 19:1-70.
29—International patent application WO93/18150.
30—International patent application WO99/53310.
31—International patent application WO98/04702.
32—International patent application WO02/02606.
33—Kalman et al. (1999) *Nature Genetics* 21:385-389.
34—Read et al. (2000) *Nucleic Acids Res* 28:1397-406.
35—Shirai et al. (2000) *J. Infect. Dis.* 181 (Suppl 3):S524-S527.
36—International patent application WO99/27105.
37—International patent application WO00/27994.
38—International patent application WO00/37494.
39—International patent application WO99/28475.
40—Ross et al. (2001) *Vaccine* 19:4135-4142.
41—McMichael (2000) *Vaccine* 19 Suppl 1:S101-107.
42—Schuchat (1999) *Lancet* 353 (9146):51-6.
43—International patent application WO02/34771.
44—Dale (1999) *Infect Dis Clin North Am* 13:227-43, viii.
45—Ferretti et al. (2001) *PNAS USA* 98:4658-4663.
46—Kuroda et al. (2001) *Lancet* 357(9264):1225-1240; see also pages 1218-1219.
47—*J Toxicol Clin Toxicol* (2001) 39:85-100.
48—Demicheli et al. (1998) *Vaccine* 16:880-884.
49—Stepanov et al. (1996) *J. Biotechnol* 44:155-160.
50—Bell (2000) *Pediatr Infect Dis J.* 19:1187-1188.
51—Iwarson (1995) *APMIS* 103:321-326.
52—Gerlich et al. (1990) *Vaccine* 8 Suppl:S63-68 & 79-80.
53—Hsu et al. (1999) *Clin Liver Dis* 3:901-915.
54—Sutter et al. (2000) *Pediatr Clin North Am* 47:287-308.
55—Zimmerman & Spann (1999) *Am Fam Physician* 59:113-118, 125-126.
56—Dreesen (1997) *Vaccine* 15 Suppl:S2-6.
57—*MMWR Morb Mortal Wkly Rep* 1998 Jan. 16; 47 (1):12, 19.
58—Ingram (2001) *Trends Neurosci* 24:305-307.
59—Rosenberg (2001) *Nature* 411:380-384.
60—Moingeon (2001) *Vaccine* 19:1305-1326.
61—Ramsay et al. (2001) *Lancet* 357 (9251):195-196.
62—Lindberg (1999) *Vaccine* 17 Suppl 2:S28-36.
63—Buttery & Moxon (2000) *J R Coll Physicians Lond* 34:163-168.
64—Ahmad & Chapnick (1999) *Infect Dis Clin North Am* 13:113-133, vii.
65—Goldblatt (1998) *J. Med. Microbiol.* 47:563-567.
66—European patent 0 477 508.
67—U.S. Pat. No. 5,306,492.
68—International patent application WO98/42721.
69—*Conjugate Vaccines* (eds. Cruse et al.) ISBN 3805549326, particularly vol. 10:48-114.
70—Hermanson (1996) *Bioconjugate Techniques* ISBN: 0123423368 or 012342335X.
71—European patent application 0372501.
72—European patent application 0378881.
73—European patent application 0427347.
74—International patent application WO93/17712.
75—International patent application WO98/58668.
76—European patent application 0471177.
77—International patent application WO00/56360.
78—International patent application WO00/61761.
79—Robinson & Torres (1997) *Seminars in Immunology* 9:271-283.
80—Donnelly et al. (1997) *Annu Rev Immunol* 15:617-648.
81—Scott-Taylor & Dalgleish (2000) *Expert Opin Investig Drugs* 9:471-480.
82—Apostolopoulos & Plebanski (2000) *Curr Opin Mol Ther* 2:441-447.
83—Ilan (1999) *Curr Opin Mol Ther* 1:116-120.
84—Dubensky et al. (2000) *Mol Med* 6:723-732.
85—Robinson & Pertmer (2000) *Adv Virus Res* 55:1-74.
86—Donnelly et al. (2000) *Am J Respir Crit Care Med* 162 (4 Pt 2):S 190-193.
87—Davis (1999) *Mt Sinai J Med* 66:84-90.
88—Gennaro (2000) *Remington: The Science and Practice of Pharmacy*. 20th edition, ISBN:0683306472.
89—WO93/13202.
90—International patent application WO01/64922.
91—International patent application filed 26 Jul. 2002 under attorney reference P027797WO in the name of CHIRON SpA claiming priority from UK patent applications 0118401.9, 0121591.2 and 0211025.2.
92—International patent application WO01/64920.
93—UK patent application 0121591.2.
94—International patent application filed 20 Jun. 2002 under attorney reference P027504WO in the name of CHIRON SpA claiming priority from UK patent application 0115176.0.

The invention claimed is:

1. A composition comprising an antigen, an aluminium salt and histidine, said composition further comprising at least about 2.5 mM of free phosphate, wherein said composition has a histidine to free phosphate molar ratio of at least 1.25:1.

2. The composition of claim 1, wherein the antigen is a protein antigen or a saccharide antigen.

3. The composition of claim 1 or claim 2, wherein the antigen is a bacterial antigen selected from the group consisting of:
a protein antigen from *N. meningitidis*;
an outer-membrane vesicle (OMV) preparation from *N. meningitidis*;
a saccharide antigen from *N. meningitidis*;
a saccharide antigen from *Streptococcus pnemnoniae*;
an antigen from *Bordetella pertussis*;
a diphtheria antigen;
a tetanus antigen;
a protein antigen from *Helicobacter pylori*;
a saccharide antigen from *Haemophilus influenzae*;
an antigen from *N. gonorrhoeae*;
an antigen from *Chlamydia pneumoniae*;
an antigen from *Chiamydia trachomatis*;
an antigen from *Porphyromonas gingivalis*;
an antigen from *Moraxella catarrhalis*;
an antigen from *Streptococcus agalactiae*;
an antigen from *Streptococcus pyogenes*; and
an antigen from *Staphylococcus aureus*.

4. The composition of claim 3, wherein the antigen is from *Neisseria menningitidis* serogroup B.

5. The composition of claim 2, wherein the saccharide antigen is a conjugated oligosaccharide antigen.

6. The composition of claim 1, wherein the antigen is adsorbed to the aluminium salt.

7. The composition of claim 6, wherein the aluminium salt is a hydroxide or a phosphate, or a mixture of two or more of said salts.

8. The composition of claim 1, wherein aluminium salt is aluminium hydroxyphosphate and the antigen is an acidic antigen.

9. The composition of claim 1, wherein the concentration of histidine is between about 5 mM and about 10 mM.

10. The composition of claim 1, further comprising a sodium salt.

11. The composition of claim 10, wherein the concentration of the sodium salt is between about 2.5 mM and about 5 mM.

12. The composition of claim 1, wherein the pH of the composition is between 6 and 7.

13. The composition of claim 1, further comprising a pharmaceutically acceptable carrier.

14. The composition of claim 1, comprising more than one antigen.

15. The composition of claim 14, wherein more than one of the antigens is adsorbed to an aluminium salt.

16. The composition of claim 14 or claim 15, comprising 2, 3, 4, 5, 6 or 7 of the following: an antigen from *Bordetella pertussis*; a diphtheria antigen; a tetanus antigen; an antigen from hepatitis B virus; a saccharide antigen from *Haemophilus influenzae*; inactivated polio virus; and a saccharide antigen from *N. meningitidis* serogroup C.

17. A method for raising an immune response in a mammal comprising the step of administering an effective amount of the composition of claim 1.

18. The method of claim 17, wherein the mammal is a human.

19. A process for producing an antigenic composition having improved stability, the process comprising admixing one or more antigens, an aluminium salt and histidine, wherein histidine is present during adsorption of the one or more antigens to the aluminum salt.

20. The process of claim 19, wherein the admixing comprises: a first step of admixing (i) the aluminium salt and (ii) histidine, to give a histidine/aluminium salt admixture; and a second step of admixing (i) said histidine/aluminium salt admixture and (ii) one or more antigens.

21. The process of claim 20, wherein the antigenic composition is combined with another antigenic composition.

22. A vaccine comprising the composition of claim 1 and a pharmaceutically acceptable carrier or excipient.

23. The composition of claim 1 comprising from about 2.5 mM to about 5 mM of free phosphate.

24. The composition of claim 7, wherein the aluminium salt is aluminum oxyhydroxide, aluminum hydroxyphosphate, or a mixture of two or more of said salts.

25. The composition of claim 10, wherein the sodium salt is sodium phosphate.

26. A composition comprising a nucleic acid encoding a protein antigen, an aluminium salt and histidine, said composition further comprising at least about 2.5 mM of free phosphate, wherein said composition has a histidine to free phosphate molar ratio of at least about 1.25:1.

27. A method for raising an immune response in a mammal, the method comprising administering to said mammal a composition comprising a mixture of antigens, essentially a single aluminium salt, and histidine, wherein said single aluminum salt is present in a ratio of at least 100:1 relative to any other aluminum salt in the composition.

28. The method of claim 27, wherein the single aluminum salt is an aluminum hydroxide or an aluminum phosphate.

29. The method of claim 28 wherein the single aluminum salt is aluminum oxyhydroxide or aluminum hydroxyphosphate.

30. The method of claim 27, wherein the histidine has a concentration between 1 mM and 10 mM.

* * * * *